United States Patent [19]

Nies et al.

[11] Patent Number: 6,118,043
[45] Date of Patent: Sep. 12, 2000

[54] BONE REPLACEMENT MATERIAL WITH FGF

[75] Inventors: Berthold Nies; Elvira Dingeldein; Helmut Wahlig, all of Darmstadt, Germany

[73] Assignee: Merck Patent Gesellschaft mit Beschrankter Haftung, Germany

[21] Appl. No.: 08/475,435

[22] Filed: Jun. 7, 1995

Related U.S. Application Data

[63] Continuation of application No. 07/904,089, Jun. 25, 1992, abandoned.

[30] Foreign Application Priority Data

Jun. 26, 1991 [DE] Germany ................ 41 21 043

[51] Int. Cl.[7] .................. A61F 2/00; A61F 2/02; A61F 2/30
[52] U.S. Cl. ................ 623/16; 424/422; 424/423; 424/424; 424/425; 424/426
[58] Field of Search ............ 623/16; 424/422–426

[56] References Cited

U.S. PATENT DOCUMENTS

| | | | |
|---|---|---|---|
| 4,233,217 | 11/1980 | Shetty | 260/239 |
| 4,979,959 | 12/1990 | Guire | 623/66 |
| 5,073,114 | 12/1991 | Detsch | 433/228.1 |
| 5,077,049 | 12/1991 | Dunn et al. | 424/426 |

FOREIGN PATENT DOCUMENTS 0 326 907  8/1989  European Pat. Off. .

OTHER PUBLICATIONS

"Fibroblast growth factor stimulates bone formation", Aspenberg et al., *Acta Orthop. Scand.*, vol. 60(4), 1989, pp. 473–476.

"Fibroblast growth factor in chick osteogenesis", Frenkel et al., *Biomaterials*, vol. 11, 1990, pp. 38–40.

*Primary Examiner*—Mickey Yu
*Assistant Examiner*—Choon P. Koh
*Attorney, Agent, or Firm*—Millen, White, Zelano & Branigan, P.C.

[57] ABSTRACT

The invention relates to a bone replacement material which comprises one or more polypeptides having the biological action of fibroblast growth factors in a porous matrix. The healing-in properties correspond to those of autologous bone transplantation.

25 Claims, No Drawings

BONE REPLACEMENT MATERIAL WITH FGF

This is a continuation of application Ser. No. 07/904,089 filed Jun. 25, 1992, now abandoned.

SUMMARY OF THE INVENTION

The invention relates to bone replacement materials which comprise one or more polypeptides having the biological action of fibroblast growth factors in a porous matrix.

Bone replacement materials are to be understood as materials which can be used as implants for replacing or reconstituting bone structures because of defects following disease—or accident-related surgical intervention. Examples which may be mentioned are shaped implant articles, such as bone prostheses of the most diverse type, bone-joining elements, for example in the form of medullary space nails, bone screws and osteosynthesis plates and implant materials for filling spongiosa bone defects or tooth extraction cavities and for plastic surgery of contour defects in the jaw/face region.

Those implant materials which have a high bioactivity, that is to say to the extent that they are accepted in the organism and integrated into it, are regarded as particularly favorable for the healing-in process. In the case of bone replacement material, this means that it should soon fuse firmly and permanently with endogenous tissue, in particular with the bone.

It is known that the most favorable healing-in results have hitherto been achieved in practice only with endogenous materials, that is to say with bone transplants. The availability of bone transplants is of course limited. Autologous transplants, that is to say transplants from the same individual, can be removed, if they are present at all in a suitable shape and quantity, only by at least one additional surgical intervention, which in turn necessitates an additional healing process at the removal site. The same also applies in principle to homologous transplants, that is to say transplants from donor individuals of the same species. These are also accompanied by problems of compatibility, and also the risk of infection with viruses, such as, in particular, hepatitis and HIV viruses, which still cannot be excluded completely at present. The storage of donor material in bone banks is furthermore expensive and in the end of only limited duration.

Implant materials for bone replacement from synthetic materials not related to the body or from materials related to the body can display bioinert to bioactive properties, depending on their nature and state. However, the healing-in results of endogenous bone transplants have not yet been achieved by any synthetic implant material.

An object of the invention, therefore, is to provide a bone replacement material, the biological activity of which comes as close as possible to that of endogenous bone transplantation.

Upon further study of the specification and appended claims, further objects and advantages of this invention will become apparent to those skilled in the art.

It has now been found that this is achieved by a bone replacement material which comprises one or more polypeptides having the biological action of fibroblast growth factors in a porous matrix.

The invention therefore relates to a bone replacement material which comprises one or more polypeptides having the biological action of fibroblast growth factors in a porous matrix.

The invention particularly relates to such a bone replacement material in which the porous matrix is a mineral matrix, preferably based on calcium minerals.

Fibroblast growth factors (FGF), which belong to the class of endogenous peptide growth factors, were originally detected as substances in the brain and hypophysis and isolated therefrom and displayed an activity which promotes the growth of fibroblasts. FGFs are known as active angiogenic factors which are responsible, inter alia, for neovascularization during wound healing. Further details on FGFs, including their modification products, on their isolation or preparation, their structure, their biological activities and mechanisms thereof and on corresponding medical uses can meanwhile be found in extensive technical literature. A comprehensive review is offered, for example, by A. Baird and P. Böhlen, Fibroblast Growth Factors, in: Peptide Growth Factors and their Receptors I (editors: M. B. Sporn and A. B. Roberts) Springer Verlag Berlin, Heidelberg, New York 1990.

In addition to an abundance of positive actions of FGFs in widely varying fields of indication, influences of FGFs in osteogenesis have also recently been reported in individual cases, for example in Biomaterials 11, 38–40 (1990). It is reported in Acta Orthop. Scand. 60, (4) 473–476 (1989) that an increased content of mineralized tissue was found in implants of demineralized bone matrix (DBM) which had been charged with recombinant human basic FGF and implanted intramuscularly into rats. DBM is known per se as a bone growth-promoting substance, since it contains itself still intact endogenous factors of the most diverse type having a bone growth-promoting activity. However, the biological activity of DBM varies according to its origin and pretreatment and can in no way be standardized to a reproducible level. DBM is moreover unsuitable in practice as an implant material for bone replacement because of a lack of mechanical strength. From the findings published, it was in no way to be deduced that a material which combines the mechanical properties of synthetic implant materials with the biological activity which only bone transplants have could be provided by the bone replacement material according to the invention.

The bone replacement materials according to the invention are characterized by the common feature that they comprise one or more polypeptides having the biological action of FGF in a porous matrix. Not only the "classical" FGFs, such as acidic fibroblast growth factor (aFGF) and basic fibroblast growth factor (bFGF), but also all peptidic growth factors which display the biological action of FGF are thus to be regarded as growth factors which are suitable according to the invention.

Protocols for determining the display of biological action of FGF of the peptides are found in Baird et al., supra, and the references described below.

The narrower sector of FGFs includes natural FGFs, in particular of bovine and human origin, as well as FGFs prepared by recombinant methods. Human aFGF and bFGF prepared by recombinant methods are particularly preferred. Further details on bovine and human aFGFs and bFGFs prepared by recombinant methods can be found, for example, in the following patent documents: EP 228 449, EP 248 819, EP 259 953 and EP 275 204, the entire disclosures of which are hereby incorporated by reference. The wider sector of FGFs also includes muteins, which differ from aFGF and bFGF to a certain extent in the number and/or sequence of the amino acids, without this being associated with a substantial change in action. Examples are found specifically in EP 326 907, e.g., bFGFs in which cysteine moieties are replaced by serine moieties. The wider sector of FGFs finally also includes related peptides with sometimes significantly different amino acid sequences and with the action of FGF as well as with an activity which intensifies the action of FGF. The following patent documents may be mentioned as examples of literature references: EP 148 922, EP 226 181, EP 281 822, EP 288 307, EP 319 052, EP 326 907, and WO 89-12645, the entire disclosures of which are hereby incorporated by reference.

FGFs in the context of the invention furthermore include derivatives of these peptides which are obtained with stabilizing and/or activity-increasing agents. These are, in particular, forms of aFGF and bFGF which are stabilized towards acid and contain as stabilizing agents, for example, glycosamine-glycans, such as heparin, heparin fragments, heparan sulfate and dermatan sulfate, or glucan sulfates, such as dextran sulfate and cyclodextrin sulfate. FGF derivatives of this type are described, for example, in EP 251 806, EP 267 015, EP 312 208, EP 345 660, EP 406 856, EP 408 146, WO 89-12464, WO 90-01941 and WO 90-03797. the disclosures of which are hereby incorporated by reference.

Forms of human bFGF prepared by recombinant methods, such as are described in EP 248 819, are particularly preferred for use in the bone replacement materials according to the invention.

The FGFs can be present in the bone replacement materials according to the invention in a concentration of 1 ng/cm$^3$–1 mg/cm$^3$. The choice of concentration within the range mentioned can depend on the nature and form and the activity of the FGF to be employed in the individual case., and on the nature of the implant material proposed in the individual case and its possibly inherently present bioactivity. The concentration of FGF is preferably in the range between 1 $\mu$g/cm$^3$ to 100 $\mu$g/cm$^3$.

All the known and customary implant materials can in principle be present in the bone replacement materials according to the invention if they are or have a porous matrix for accommodation of FGF. Implant materials can be classified into the classes of mineral, in particular ceramic materials, physiologically acceptable metallic materials, physiologically acceptable polymer materials and composite materials of two or more materials of the type mentioned. These materials can form a porous matrix as an entirety, for example in the form of porous shaped implant articles, or it is possible for only certain components of the material to be in the form of porous material or for certain regions of a shaped implant material to be a porous matrix. The last two cases can be realized, for example, in the form in which a composite material or a bone cement contains a porous component, or an implant is provided with a porous surface coating or an appropriately roughened surface.

On the materials side, preferred materials for the bone replacement materials according to the invention are those which are mineral and in particular ceramic in nature. One advantageous aspect of the invention is that materials which are bioinert per se, such as, for example, oxido-ceramic materials, can be activated biologically by being charged with FGF and in this way exhibit significantly better growing-in and healing-in properties.

Nevertheless, preferred mineral materials are those which are bioactive per se. This chiefly applies to materials which are based on calcium-containing materials, such as, in particular, calcium carbonate, calcium phosphates and systems derived from these compounds. From the group of calcium phosphates, hydroxyapatite, tricalcium phosphate and tetracalcium phosphate are to be mentioned as preferred.

However, mineral-based implant materials usually guarantee a high mechanical stability only if they are employed as ceramics, that is to say in the form of materials or workpieces sintered at sufficiently high temperatures.

Bone replacement materials based on calcium phosphate ceramics, because these are related chemically to the mineral phase of natural bone, are bioactive. Natural bone chiefly consists in its mineral phase of hydroxyapatite, a calcium phosphate having the empirical formula $Ca_5(PO_4)_3OH$.

Hydroxyapatite of synthetic or organic origin, for example from natural bone material, is therefore a frequently used raw material for the production of implants for bone replacement. Hydroxyapatite ceramic is largely non-absorbable in the organism. This means that exogenous material is retained practically unchanged for a long period and integration into the organism takes place essentially by fusion with existing and regenerating bone and by growing into the surrounding tissue.

Under certain circumstances, tricalcium phosphate is absorbable in the organism. Tetracalcium phosphate is essentially non-bioabsorbable.

Porous calcium phosphate ceramics exhibit particularly favorable growing-in properties. Particularly preferred materials here are those based on natural bone, which is mineralized by various treatments and converted into a ceramic system, in which the structure of the bone, should be retained as far as possible. The processes have the common feature of the removal of the organic bone constituents and subsequent compaction to a ceramic by sintering at appropriate temperatures. Organic contents are removed by chemical solution processes or by pyrolytic processes.

Further details on bone ceramics and particularly favorable processes for their preparation can be found, for example, in the patent documents DE 37 27 606 (corresponding to U.S. Ser. No. 07/458,710), DE 39 03 695 (corresponding to U.S. Ser. No. 07/476,207), DE 41 00 897 and DE 40 28 683 (corresponding to U.S. Ser. No. 07/756, 744), the entire disclosures of which are hereby incorporated by reference.

Because of their excellent agreement with the pore system of natural bone, bone ceramic implants show considerable biological advantages in growing-in properties and healing in the organism. Spongiosa bone ceramic is particularly preferred because of its high-porosity, three-dimensionally open-pored network structure.

Shaped articles of ceramic material, in particular of the abovementioned type, are employed primarily for replacing load-bearing bone structures which must withstand high mechanical stresses. Examples of these are bone prostheses and bone-joining elements, such as, for example, medullary space nails, bone screws and osteosynthesis plates.

More precise clinical studies have shown that exposed mineral contact surfaces in implants of calcium phosphate ceramic preferentially stimulate regeneration of mineral bone matrix, resulting in a firm fusion of the implant. This is promoted still further in the case of porous implants, where a particularly intensively interlinked and therefore mechanically stable fusion develops because of the higher surface area and by new bone tissue forming shoots into the implant. In the case of implant materials of mainly polymeric materials or of bioinert materials, connective tissue is initially preferentially formed instead, leading to only a moderately firm fusion.

It has now been found that, due to being charged with FGF, the bone replacement materials according to the invention, largely independently of the nature of the material, stimulate considerable regeneration of mineral bone matrix in the contact region and, depending on whether bone can grow through them because of porosity and/or absorption, also inside the matrix after implantation. This stimulation is in all cases significantly higher than in the case of corresponding non-charged implants. A pronounced synergistic effect was to be observed here in the case of porous implants charged with FGF and based on calcium minerals, in particular calcium phosphate ceramics. In preclinical model experiments on bone ceramic implants charged with FGF, complete incorporation into the bone by regenerated, chiefly mineralized bone matrix growing in and through was found six weeks after implantation. A comparable result was achieved only by autologous bone transplants, while, for example in the case of uncharged bone ceramic, DBM and DBM-impregnated bone ceramic, fusion by regeneration of bone matrix was to be found only in the contact regions with the existing bone. It is assumed that the bone growth-promoting action of FGF and the bioactivity of calcium-containing implant materials, such as, in particular, bone ceramic, mutually intensify each other and in this way lead to an accelerated healing-in and incorporation of the implant.

The positive influence of FGF on the healing-in properties of implants for bone replacement can be applied, as already mentioned, to practically all types of bone replacement materials and implant materials if these are of a type and shape such that they have a porous matrix for accommodation of FGF and re-release to the organism, expediently at least chiefly in the contact region with the body tissue. These requirements are also met, for example, by implants of metallic materials which are in themselves porous or have a porous surface coating, preferably of bioactive hydroxyapatite, or which have a surface which has a porous structure or is at least roughened. The same applies to implants of polymeric materials, other ceramic materials or composite materials.

The bone replacement materials according to the invention can in principle be present not only as shaped implant articles, but also in powder or granule form, depending on what is required by the site of use and the intended use.

Preferred possible composite materials are those in which at least one component is present as a porous matrix for accommodation of FGF. Corresponding bone replacement materials based on composite materials in which a porous mineral matrix is present in powder or granule form and forms a shaped article in association with a physiologically acceptable polymeric active compound are expedient. Composite materials of this type are to be found in the relevant technical literature, for example Patent Documents WO 90-01342 and WO 90-01955, the entire disclosures of which are hereby incorporated by reference, in which implant materials based on calcium phosphate particles or bone ceramic particles and bioabsorbable polymer are described.

The bioactivity of bone cements can also be increased in an analogous manner. Bone cements consist mainly of acrylate systems comprising mineral fillers, usually based on calcium compounds. According to the invention, for example, FGF-charged porous hydroxyapatite powder or granules can be employed as a filler component in bone cement.

The acrylate systems are fully conventional in the art and are usually based on methylmethacrylate. Additional information is found in U.S. Pat. No. 4,233,217, the entire disclosure of which is hereby incorporated by reference.

The preparation of the bone replacement materials according to the invention by charging the particular porous matrix with polypeptides having the action of FGF presents no problems in itself. A procedure is expediently followed in which a suitable liquid or semi-liquid preparation of FdF, for example in the form of a buffered aqueous solution, a suspension or a gel, is used as the starting substance and is allowed to soak completely, in the proposed dosage, into the porous matrix of the bone replacement material. The bone replacement material is then, or after any drying which may be necessary, already usable or can be stored in accordance with the safety precautions required for such materials for medical use. The porous implants, under sterile conditions, are soaked with FGF solution, freeze dried, and packaged in, e.g., conventional deep drawn packings. See, e.g., Example 3. Porous-shaped implant articles, preferably of bone ceramic, implants provided with a porous surface and porous particulate components for composite materials and bone cements can be charged with FGF in this manner.

In a preferred embodiment, the bone replacement material according to the invention is in the form of a ready-to-use implantation set of two or more separate components, in which one component comprises the porous matrix and another component comprises a solution of the polypeptide having the action of FGF. Such an embodiment is particularly appropriate in order effectively to counteract possible stability problems which could arise during long-term storage of already made-up bone replacement materials according to the invention. Thus, for example, it is reported in the technical literature that calcium ions, which are indeed present in the materials preferred here, can have a destabilising influence on FGF. The bone replacement materials according to the invention are used in the form of an implantation set of this type such that the porous matrix of the particular implant material is charged with the FGF-containing solution in the manner described above shortly before or during the surgical intervention for the implantation. Such an embodiment is particularly expedient in the case where the porous matrix is formed by a shaped implant article itself, mineral, preferably ceramic, materials and in particular sintered bone ceramic being primarily suitable as the material.

Depending on the embodiment, the bone replacement material according to the invention is thus an at least equivalent substitute for autologous and homologous bone transplants, or is a considerable improvement to other forms of bone replacement in respect of healing-in properties.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application P 41 21 043.3, filed Jun. 26, 1991, are hereby incorporated by reference.

EXAMPLE 1
Production of Shaped Implant Articles

Cylindrical shaped articles 10.00 mm in height and 9.55 mm in diameter are produced with a diamond milling cutter from spongiosa hydroxyapatite bone ceramic blanks prepared according to DE 40 28 683.

Some of these shaped articles are impregnated with in each case 100 μl of a solution comprising 50 μg of human bFGF prepared by a recombinant method, dried and stored at 4–6° C. until the time of implantation.

The other shaped articles are used for comparison purposes.

EXAMPLE 2

Comparative Animal Experiment Study

Animal species: Mini-pig, adult, female, 6 groups, 8 implants per group

Implants: a) spongiosa hydroxyapatite ceramic with FGF (according to Example 1)
b) spongiosa hydroxyapatite ceramic
c) DBM
d) spongiosa hydroxyapatite ceramic, impregnated with DBM
e) autologous spongiosa transplant, removed with accurate dimensions using a twin milling cutter.
f) homologous spongiosa transplant, removed with accurate dimensions using a twin milling cutter, storage at −30° C. until the time of implantation Site of implantation: Into the patellar sliding bed of the femur condylus, on the left and right After 6 weeks, the bones were removed by surgery and the bone regeneration and mineralization were determined by histological examination.

Result a) Spongiosa hydroxyapatite ceramic with FGF Bone regeneration from the bone bed up to the center of the implant; complete incorporation
b) Spongiosa hydroxyapatite ceramic Marginal osseous contact with the implant; growing-in only round the edge of the implant
c) DBM Marginal osseous contact with the implant; growing-in only round the edge of the implant
d) Spongiosa hydroxyapatite ceramic, impregnated with DBM Bone regeneration in the contact region of the bone bed and implant; amorphous DBM still present.
e) Autologous spongiosa transplant Bone regeneration from the bone bed into the center of the implant; complete incorporation
f) Homologous spongiosa transplant Bone regeneration from the bone bed, affecting about ⅓ to ½ of the implant; partial incorporation.

EXAMPLE 3

Implantation Set

Porous spongiosa hydroxyapatite bone ceramic shaped articles (according to Example 1; non-charged) are placed in deep-drawn packaging moldings of appropriate shape, the chambers of which correspond exactly to the dimensions (only slight residual volume) of the shaped articles. The deep-drawn components are sealed and sterilized, and enclosed in a wrapping.

bFGF solution is freeze-dried in citrate buffer (10 mmol; pH 5.0) after addition of sucrose solution (9%), and introduced into ampoules. The ampoule filling and ampoule volume are coordinated so that the later charging of the ceramic shaped articles corresponds to 50 μg of bFGF/cm$^3$ block volume.

Shaped implant article packs and bFGF ampoules form pack units as an implantation set. Conditioning on the operating table The bFGF solution is reconstituted in citrate buffer (pH 5.0) and then drawn up into a sterile syringe.

After the wrapping has been opened, the bFGF solution is injected through the sterile internal packaging into the deep-drawn container of the ceramic shaped article. The injection volume is measured so that the shaped article is immersed completely in the bFGF solution. After about 1 minute, excess bFGF solution is sucked back into the syringe. The ceramic shaped article retains about as much solution as corresponds to its pore volume.

The charged shaped article can be implanted after the primary packaging has been opened.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A bone replacement material consisting essentially of 1–100 μg/cm$^3$ acidic or basic fibroblast growth factor and a porous matrix consisting essentially of calcium minerals, wherein said growth factor is contained in said matrix.

2. A bone replacement material according to claim 1, wherein the growth factor is basic fibroblast growth factor.

3. A bone replacement material according to claim 1, wherein the growth factor is acid fibroblast growth factor.

4. A bone replacement material according to claim 1, wherein the growth factor is recombinant.

5. A bone replacement material according to claim 1, wherein the growth factor is a mutein of fibroblast growth factor.

6. A bone replacement material according to claim 1, wherein the growth factor is acid-stabilized forms of fibroblast growth factor.

7. A bone replacement material according to claim 1, wherein said porous matrix essentially consists of calcium phosphate.

8. A bone replacement material according to claim 1, wherein said porous mineral matrix consists of one or more calcium minerals selected from the group consisting of hydroxyapatite, tricalcium phosphate, and tetracalcium phosphate.

9. A bone replacement material according to claim 8, wherein the calcium minerals are obtained from natural bone.

10. A bone replacement material according to claim 1, wherein said porous matrix is sintered calcium phosphate ceramic.

11. A bone replacement material according to claim 1, wherein said porous matrix consists of sintered spongiosa bone ceramic.

12. A bone replacement material according to claim 1, wherein said porous matrix is formed by a physiologically acceptable metallic material.

13. A bone replacement material according to claim 1, wherein said matrix is formed by a physiologically acceptable polymer material.

14. A bone replacement material according to claim 1, wherein said matrix is present as a shaped implant article.

15. A bone replacement material according to claim 1, wherein the matrix forms the surface of a surface coating of a shaped implant article.

16. A bone replacement material according to claim 1, wherein said matrix is present in powder or granule form.

17. A bone replacement material according to claim 1, wherein said matrix is present in powder or granule form and forms a shaped article in association with a physiologically acceptable polymeric material.

18. A bone replacement material according to claim 1, wherein said matrix is present in powder or granule form and forms a component of a bone cement.

19. A bone replacement material according to claim 1, wherein said material is present in the form of a ready-to-use implantation set of two or more separate components, one component of which comprises said porous matrix and another component of which comprises a solution or suspension of said fibroblast growth factor.

20. A bone replacement material according to claim 1, wherein the component which comprises said porous matrix is a shaped implant article.

21. A bone replacement material according to claim 20, wherein the shaped implant article consists of a mineral material.

22. A bone replacement material according to claim 21, wherein said shaped implant article consists of sintered bone ceramic.

23. A bone replacement material according to claim 21, wherein the mineral is a ceramic material.

24. A bone replacement material according to claim 1, wherein said mineral is a bioactive material.

25. A bone replacement material of claim 1, wherein said growth factor is in an amount effective to stimulate bone growth.

* * * * *